(12) United States Patent
Barrett et al.

(10) Patent No.: US 8,034,058 B2
(45) Date of Patent: Oct. 11, 2011

(54) TIBIAL CEMENT SKIRT ASSEMBLY

(75) Inventors: David Barrett, Southhampton (GB);
Andrew New, Southhampton (GB);
John Ewans, High Wycombe (GB);
Rick Kowalski, Preston (GB)

(73) Assignee: Depuy International Limited (GB)

( * ) Notice: Subject to any disclaimer, the term of this patent is extended or adjusted under 35 U.S.C. 154(b) by 1551 days.

(21) Appl. No.: 11/378,834

(22) Filed: Mar. 17, 2006

(65) Prior Publication Data

US 2006/0259149 A1 Nov. 16, 2006

(30) Foreign Application Priority Data

Mar. 17, 2005 (GB) .................................. 0505484.6
Aug. 24, 2005 (GB) .................................. 0517284.6

(51) Int. Cl.
*A61F 2/38* (2006.01)
(52) U.S. Cl. ...................... 606/92; 623/20.14
(58) Field of Classification Search .............. 606/92–95, 606/86 R, 99, 87–88, 96, 79, 90; 623/20.14–20.36; 24/298, 300–302
See application file for complete search history.

(56) References Cited

U.S. PATENT DOCUMENTS

| | | | | |
|---|---|---|---|---|
| 4,034,418 A | * | 7/1977 | Jackson et al. ............... | 623/20.3 |
| 4,274,163 A | | 6/1981 | Malcom | |
| 4,711,233 A | | 12/1987 | Brown | |
| 4,944,757 A | * | 7/1990 | Martinez et al. ........... | 623/20.15 |
| 4,997,448 A | * | 3/1991 | Filer ............................. | 623/23.2 |
| 5,037,425 A | * | 8/1991 | Brown ........................... | 606/92 |
| 5,047,061 A | * | 9/1991 | Brown ......................... | 623/23.2 |
| 5,062,852 A | * | 11/1991 | Dorr et al. ................... | 623/20.33 |
| 5,171,276 A | * | 12/1992 | Caspari et al. ............. | 623/16.11 |
| 5,480,450 A | | 1/1996 | James | |
| 5,500,018 A | | 3/1996 | Spotorno | |
| 5,683,471 A | * | 11/1997 | Incavo et al. ................. | 128/898 |
| 5,876,460 A | * | 3/1999 | Bloebaum ................. | 623/16.11 |
| 5,951,563 A | | 9/1999 | Brown | |
| 6,179,876 B1 | | 1/2001 | Stamper | |
| 6,893,445 B1 | * | 5/2005 | Revie et al. ..................... | 606/94 |
| 2002/0133230 A1 | * | 9/2002 | Repicci ....................... | 623/14.12 |

(Continued)

FOREIGN PATENT DOCUMENTS

CH 685423 A5 1/1991

(Continued)

OTHER PUBLICATIONS

UK Search Report dated Jun. 29, 2005.
EP Search Report EP 06 25 1430 Dated Feb. 20, 2009.

*Primary Examiner* — Eduardo C Robert
*Assistant Examiner* — Jan Christopher Merene

(57) ABSTRACT

An assembly for use in fixing a first component of a joint prosthesis, having a bone facing surface and an exposed surface which faces towards a second component of the joint prosthesis when implanted on a patient's bone. The assembly includes a skirt which can be temporarily fixed to the edge of the first component extending along the edge thereof from a remote portion of the edge to an accessible portion of the edge. The skirt provides at least one opening through which cement located between the bone facing surface of the component and the surface of the bone can be displaced. The opening is located so that cement is prevented from being displaced at the remote portion of the edge and is instead displaced at the accessible portion of the edge.

4 Claims, 6 Drawing Sheets

U.S. PATENT DOCUMENTS

| | | | |
|---|---|---|---|
| 2003/0100953 A1* | 5/2003 | Rosa et al. | 623/20.3 |
| 2004/0015238 A1 | 1/2004 | Buehler | |
| 2004/0193170 A1* | 9/2004 | Kemppainen et al. | 606/92 |
| 2006/0004375 A1* | 1/2006 | Watkins et al. | 606/94 |

FOREIGN PATENT DOCUMENTS

| | | |
|---|---|---|
| JP | 5123333 A | 5/1993 |
| WO | WO 0025700 A2 | 5/2000 |
| WO | WO 2004026191 A1 | 4/2004 |

\* cited by examiner

TIBIAL CEMENT SKIRT ASSEMBLY

CROSS REFERENCE TO RELATED APPLICATION

The present application claims the benefit, under 35 USC 119(a)-(d) of prior GB Application No. 0505484.6, filed Mar. 17, 2005 (now abandoned) and GB Application No. 0517284.6, filed Aug. 24, 2005 (now abandoned).

This invention relates to an assembly for controlling the flow of excess bone cement into a joint region during implantation of a component of a joint prosthesis.

Joint prostheses generally include first and second components which can be fixed to the bones of the articulating joint. For example, in the case of a knee joint, a joint prosthesis can include femoral and tibial components, and in the case of a shoulder joint, a prosthesis can include glenoid and humeral components. The bone engaging surface of the joint prosthesis component will often have a peg or stem portion which can extend into a cavity within the bone (generally the intramedullary cavity) and a portion which faces towards the end of the bone. It is desirable that there should be a strong fixation between the bone and the prosthesis component, on the surface of the peg or stem portion and on the surface of the component which faces towards the end of the bone.

It is common to use bone cement to achieve suitable fixation between a bone and a joint prosthesis component. Bone cement materials are generally reactive materials, which can be manipulated, and possibly flow, during the initial period after they are mixed together. The reaction after mixing leads to such materials becoming harder as they cure. An advantage of the use of a bone cement is that it can achieve fixation quickly, depending on the time taken for the cement material to cure, generally between 5 and 20 minutes.

Preferably, bone cement which is applied to the space between a prepared bone and a joint prosthesis component should be pressurised so that it penetrates porous cancellous bone tissue with which it is in contact. It is also important to ensure that there is adequate cement in that space to achieve fixation over all of the engaging surfaces of the bone and the component. For these reasons, it is established practice to provide a small excess of cement into the said space.

It is important to ensure that excess cement that is displaced from the space between a prepared bone and a joint prosthesis component does not interfere with articulation of the joint prosthesis after completion of the joint replacement procedure. For example, cement that is displaced from the joint region might be deposited on the bearing surfaces of the joint components. It might also interfere with surrounding soft tissue.

It can be difficult to inspect regions of a joint which are remote from the incision through which a procedure is being performed to determine whether cement has been displaced from the space between a prepared bone and a joint prosthesis component, and to remove any such displaced cement. Furthermore, it is generally desirable to minimise the size of the incision: this tends to increase the problem of gaining access to regions of the joint which are remote from the incision, to inspect for displaced cement and to remove any such cement.

The present invention provides an assembly for use in fixing a first component of a joint prosthesis, which includes a skirt which can be temporarily fixed to the edge of the first component extending along the edge thereof from a remote portion of the edge to an accessible portion of the edge, which provides at least one opening through which cement located between the bone facing surface of the component and the surface of the bone on which the component is to be implanted can be displaced.

Accordingly, in one aspect, the invention provides an assembly for use in fixing a first component of a joint prosthesis which includes a second component which articulates with the first component to a prepared bone, which comprises:

(a) a first component of joint prosthesis having a bone facing surface and an exposed surface which faces towards the second component of the joint prosthesis when implanted on a patient's bone, (b) a skirt which can be temporarily fixed to the edge of the first component extending along the edge thereof from a remote portion of the edge to an accessible portion of the edge, which can provide at least one opening through which cement located between the bone facing surface of the component and the surface of the bone on which the component is to be implanted can be displaced, located so that cement is prevented from being displaced at the remote portion of the edge and is instead displaced at the accessible portion of the edge.

The assembly of the invention can enable the flow of excess bone cement to be controlled during fixation of a component of a joint prosthesis. Control of the flow of the bone cement in this region help to achieve sufficient pressurisation of the bone cement to ensure penetration of pores in the bone, which can affect the strength of the fixation of the component to the bone.

The skirt can control the direction in which excess bone cement is displaced from the space between the joint prosthesis component and the bone when the component is fixed on to the bone. In particular, the cement can be directed to flow away from the remote portion of the edge of the component and towards the accessible portion of the component. This means that displaced cement can be removed from the surfaces of the component and surrounding tissue. It also reduces the likelihood of cement collecting on surfaces of the component and surrounding tissue which are not visible to the surgeon through the incision. The reduced likelihood of displaced cement being present on remote surfaces of the prosthesis component or soft tissue or both can reduce the likelihood of cement interfering with joint articulation after implantation.

Preferably, the skirt has a break off portion which can be broken off to provide the opening for displacement of cement. The break off portion can be broken off before the joint prosthesis component and the skirt are placed in contact with the resected bone. The break off portion will generally be arranged so as to provide an opening through which cement can be displaced at the accessible edge of the joint prosthesis component. For example, in the case of a procedure to replace a knee joint in which an anterior incision is made, the opening in the skirt should preferably be located so that cement is displaced anteriorly.

If one or more break off portions are left in place on the skirt until after the prosthesis component and the skirt are placed in contact with the resected bone, then this help to control the displacement of cement from the space between the prosthesis component and the bone. This can help to encourage penetration of cement into the pores in the bone when the component, with the bone cement, is initially applied to the bone.

The skirt can have at least two break off portions, which can be broken off selectively to provide respective openings for displacement of cement. This can allow the skirt to be used in different orientations or on a range of different joint prosthesis components. For example, in the case of a uni-compartmental knee joint prosthesis, the skirt might be used on a component which is to be fitted to the medial or the lateral compartment of the left knee or the right knee. The provision of two or more break off portions can allow a single skirt component to be used in any of these applications.

The skirt should be fixed to the joint prosthesis component in such a way that it can be detached from it once the component has been positioned on the bone and excess cement has been displaced from the space between the component and the bone. The connection between the skirt and the component should be sufficiently secure that the application of pressure to cement located in the space between the component and the bone (generally by applying force to the component in a direction towards the bone) does not cause the skirt to become detached from the component, allowing cement to be displaced.

The nature of the connection between the joint prosthesis component and the skirt should be such that it can resist the forces which are exerted on it by the cement when force is applied to the component towards the bone. The nature of the connection will depend at least in part on the physical characteristics of the skirt, including in particular the material that the skirt is made from. The nature of the connection should also take into account the requirement that the skirt should be capable of being detached from the joint prosthesis component and removed from the joint space.

The assembly can include a fixing component by which skirt can be fixed to the joint prosthesis component. This can have the advantage of facilitating removal of the skirt from the joint space. For example, a fixing component can comprise a strap which can be connected at or towards its ends to the skirt towards the ends thereof, and can extend across the exposed surface of the joint prosthesis component between the remote and accessible portions of its edge and can be connected at or towards its respective ends to the skirt. The skirt and the fixing component can then be fastened to one another by means of inter-engaging lugs and recesses, in which the direction in which a lug is inserted into its respective recess is preferably non-parallel, more preferably approximately perpendicular, to the direction in which pressurisation forces are exerted on the skirt by cement in the space between the component and the bone.

When the assembly includes a strap which can extend across the exposed surface of the joint prosthesis component, the component can have a groove formed in it on its exposed surface in which the strap can be fitted when extending across the upper surface of the component.

A strap fixing component can be used when the joint prosthesis component is a tibial component of a knee joint prosthesis. The strap can then extend across the exposed surface of the component. When the knee joint prosthesis is a unicondylar prosthesis, the strap can extend from an anterior portion of the edge of the tibial component to a posterior portion of the edge.

The skirt can also be attached to the joint prosthesis component by virtue of features of the skirt and the joint prosthesis component. For example, the skirt might be provided with a lip at at least one of its ends, which can be received in one or more corresponding recesses on the edge of the joint prosthesis component, so that the skirt is able to resist forces exerted on it by cement. A lip on the skirt might be located between an edge of the component and adjacent bone tissue when the component abuts bone tissue along part of its peripheral edge, for example when the component is the tibial component of a unicondylar knee joint prosthesis.

The skirt can extend around the entire peripheral edge of the joint prosthesis component so that it encircles the component. It can then be provided as a continuous band which is fitted over the component. However, it will often be preferred for the skirt to be wrapped around the component so that the opposed ends abut one another or preferably overlap. The opposed ends can then be fastened together. When the skirt extends around the entire peripheral edge of the component, it can be cut to release it from the component. However, it can be preferred for the fastened ends to be capable of being released to enable removal of the skirt from the component.

The skirt can be provided by a band which extends around the periphery of the first component, and which includes a clamp which allows the band to be tightened against the peripheral edge of the component. The clamp can comprise a lever having a surface which can act against a fixed part as the lever is moved between positions in which the band is loose and tight respectively. Such movement of the lever preferably involves movement around a fulcrum. The distance between the fulcrum and the surface where it contacts the fixed part will differ between the loose and tight positions of the lever. This can be achieved in one embodiment by mounting a lever with a rounded end eccentrically with respect to the rounded end.

The band can be in the form of a continuous loop, or it can be open and arranged so that it is connected the clamp at its two ends. It can be connected to the clamp at its ends by means of fasteners, or by means of button and hole arrangements. Removal of a band-like skirt from the component can involve releasing the band and then lifting the band off the component. Alternatively, the band can be opened, allowing it to be pulled from around the component. The band can be opened by cutting it. When it is connected to the clamp at its ends, it can be opened by releasing it from the clamp.

The skirt can also be provided by a band which extends around the periphery of the first component, and includes a driver arrangement. The driver arrangement includes an actuator and at least a first and second blocks which can fit at least partially within the band and first component. The actuator can move one block relative to the other block to adjust the tension of the band.

Preferably, the outer surface of the first block contacts the band. The outer surface of the first block is preferably curved. The inner surface of the second block preferably contacts the unicompartmental tibial component. The inner surface of the first block and the outer surface of the second block can be shaped so as to cooperatively engage with each other.

Preferably, the skirt provides an aperture through which the actuator extends. Preferably, the first block has a bore extending through it. Preferably, the aperture provided by the skirt and the bore provided by the first block are aligned. The actuator can extend through the aperture of the skirt and the bore of the first block.

The bore of the first block is preferably threaded. The actuator can comprise a bolt having a thread. Preferably, the thread of the bolt engages the thread of the bore of the first block.

The actuator can contact the outer surface of the second block to ensure that the inner surface of the second block is in contact with the unicompartmental tibial component.

Rotation of the actuator can cause the first block to be displaced along the threaded bolt of the actuator. Preferably, the first block is displaced along the actuator in a direction away from the unicompartmental tibial component. The second block is preferably maintained in contact with the unicompartmental tibial component. The distance between the inner surface of the first block and the outer surface of the second block can be varied by rotation of the actuator. Rotation of the driver to increase the distance between the first and second blocks increases the tension in the band.

Preferably, the skirt has markings on it by which the volume of a quantity of a bone cement material that is located on the bone facing surface of the first component prior to implantation can be measured. This can help to ensure that sufficient cement is applied to the space between the component and the bone to achieve fixation. It can also help to ensure that the amount of cement is no greater than a preferred upper limit, which can help to reduce the amount of cement that has to be displaced from the space between the component and the bone.

The skirt can be arranged so that the volume of the space which it defines on the bone facing surface of the first component corresponds to the volume of cement which is required to bond the component to the surface of the bone. In this arrangement, the edge of the skirt which is remote from the bone facing surface of the first component can provide a marking to allow the appropriate volume of bone cement to be measured.

The assembly of the invention can be used to provide control over the displacement of bone cement from the space between any joint prosthesis component and a bone in which the component is to be implanted. It is particularly applicable to joint prosthesis components which have a peripheral edge which engages the edge of a resected bone. For example it is applicable to the tibial component of a knee joint prosthesis, where the skirt is applied to the peripheral edge of the component, to overlap the tibia at its resected edge. The invention can be applied to components of other joint prostheses. For example, it might be applied to the humeral component of a shoulder joint prosthesis, which can have a flange which fits against the end of the resected humerus.

Conventional knee joint replacement techniques involve fitting tibial and femoral components to the prepared tibia and femur respectively. Knee joint prostheses can include an intermediate bearing component which can be fitted between the tibial and femoral components. The bearing component can be fixed relative to the tibial component (fixed bearing) or can be arranged to slide relative to the tibial component during articulation of the joint (mobile bearing). The femoral component of a knee joint prosthesis is generally formed from a hard material such as a metal (for example a titanium alloy or a cobalt chromium molybdenum alloy) or a ceramic material (for example aluminium oxide or chromium nitride) or a combination of the two. A bearing component is generally formed from a relative soft material, especially a polymeric material (for example ultrahigh molecular weight polyethylene (UHMWPE)). A tibial component which is to be used in conjunction with a bearing component is generally formed from hard materials such as those used in femoral components. When a knee joint prosthesis does not include a separate bearing component, the tibial component can be formed from a soft material, especially a polymeric material such as UHMWPE.

The present invention is applicable to the tibial components of total knee joint prostheses. It is particularly applicable to the tibial components of unicondylar knee joint prostheses. The advantages of the invention are particularly apparent in minimally invasive knee joint replacement procedures in which the incision is small. This is particularly the case in relation to unicondylar knee joint replacement. However, the invention is applicable to the tibial components of total knee joint prostheses. It is also applicable to components of other joint prostheses, for example to the glenoid and humeral components of a shoulder joint prosthesis, and to the femoral and acetabular components of a hip joint prosthesis.

Use of the assembly of the invention involves providing a quantity of a bone cement on to the bone engaging surface of the joint prosthesis component. The skirt which extends at least partially around the component reduces the tendency of the cement to flow off that surface. The component is then offered to the prepared bone through the incision and pressure is applied to encourage the cement to penetrate the pores of the exposed surface of cancellous bone. When the skirt has a portion which can be broken off to form an opening, the skirt can be broken off before the component is offered to the prepared bone. However, it can be preferable to offer the component to the bone while the break off portion is broken away from the skirt, so that the tendency for cement to be displaced from the space between the component and the bone is minimised. When the skirt has more than one break off portion, the one which is closest to the incision when the component is in place on the bone is selected for removal.

Once the break off portion of the skirt has been removed (when the skirt initially had such a portion), continued application of force to the component causes excess bone cement to be displaced from the space between the component and the bone through the opening in the skirt, in a direction generally towards the incision through which the procedure is being performed. The excess bone cement is then removed from the joint region. The dimensions of the aperture in the anterior face of the skirt are determined by the viscosity and volume of the bone cement present during fixation of the tibial component.

The skirt should be formed from one or more materials having physical properties which enable it to withstand forces which are exerted on it by cement which is displaced from the space between the bone and the component. The skirt should also be capable of being removed from the joint space after the cement has cured sufficiently for it no longer to be likely to be displaced. Relevant physical properties include tensile strength and flexibility. The skirt should not deform (especially stretch) when subjected to forces resulting from pressurisation of the cement. However, it should be capable of deforming (generally in a bending mode) during removal from the joint space.

The thickness of the skirt will be selected to ensure that the skirt has the structural properties which are required for it to perform satisfactorily. The thickness that is required will also depend on the material which is used, consistent with it having the required structural properties. Preferably the skirt has a thickness of not more than about 3 mm, more preferably not more than about 2 mm, especially not more than about 1 mm, for example about 0.5 mm. The thickness of the skirt will generally be at least about 0.25 mm.

The depth of the skirt is determined by the dimensions of the cement mantle which is to be provided on the surface of the head of the bone with which the skirt is in contact and the space that is available around the joint. It will generally be appropriate for the depth of the skirt to be not more than about 20 mm, more preferably not more than about 15 mm. Preferably, the depth of the skirt is at least about 6 mm, more preferably at least about 9 mm. In a preferred embodiment, the depth of the skirt can be about 12 mm. The dimensions of the apertures present in the skirt are determined by the height of the skirt, the area of the anterior and lateral regions of the skirt and the requirement to subject the bone cement to positive pressure. For example, if the bone cement is of high viscosity it would be preferable to have more than one aperture in the anterior and/or lateral sections of the skirt in order to allow excess bone cement to be displaced at a desired rate.

The skirt can be formed using an extrusion technique, or by moulding (including casting). Features of the skirt can be formed in processing techniques such as bending, forming and cutting.

The skirt can be reinforced by one or more reinforcing webs, generally on its external surface.

Suitable rigid materials can include polymers and metals such as those which are commonly used in surgical assemblies. Suitable polymers might include polyolefins (especially polyethylenes and polypropylenes), polyethersulphones, polyetheretherketones, polycarbonates, polyesters and polyamides. Suitable metals might include certain stainless steels.

It can be preferred for the surface of the skirt which faces towards the bone when the assembly is in use to be provided by a layer of release material. Suitable materials include certain silicones.

A skirt can have at least one point of weakness formed in it to facilitate removal. The point of weakness can allow the skirt to be deformed or to break. For example, the skirt might bend at the point of weakness. The skirt can break into two or more parts. This can be particularly advantageous when the skirt is formed from a relatively rigid material which might not otherwise be capable of being removed easily from the joint space, for example without damaging the implanted joint prosthesis component or adjacent tissue or both. The point of weakness will generally be a point at which there is reduced quantity of the material of the skirt. For example, the wall thickness of the skirt can be locally reduced, for example by formation of a groove or of a series of indentations. They can be formed in the skirt by a machining operation or as a part of a moulding operation.

It is particularly preferred that the skirt is formed with a line of weakness which extends between the edge which faces away from the bone engaging surface of the prosthesis component and the opposite edge which is located adjacent to or in contact with that surface. The line of weakness can extend generally perpendicular to the bone engaging surface of the prosthesis component.

The skirt may be composed of a flexible material such as a silicone rubber. Preferably the skirt may be supported by a supporting frame positioned outside the wall member. For example, the skirt can comprise a resiliently deformable membrane which can be located around the prepared bone. The deformability of the membrane can enable it to conform to the shape and size of the bone, to provide an appropriately shaped cement mantle around the bone. This provides the additional advantage that the flexibility of the skirt ensures a tighter fit around the bone and therefore provides for complete elimination of excess bone cement flow in the posterior region of the joint.

When a skirt composed of a flexible material is removed from the tibial component the posterior section of the skirt will flex so as to follow the shape of the external edge of the tibial component. The flexible skirt may therefore be removed from the fixed tibial component in one action by the surgeon.

Embodiments of the invention will now be described by way of example with reference to the accompanying drawings, in which.

Figure 1:
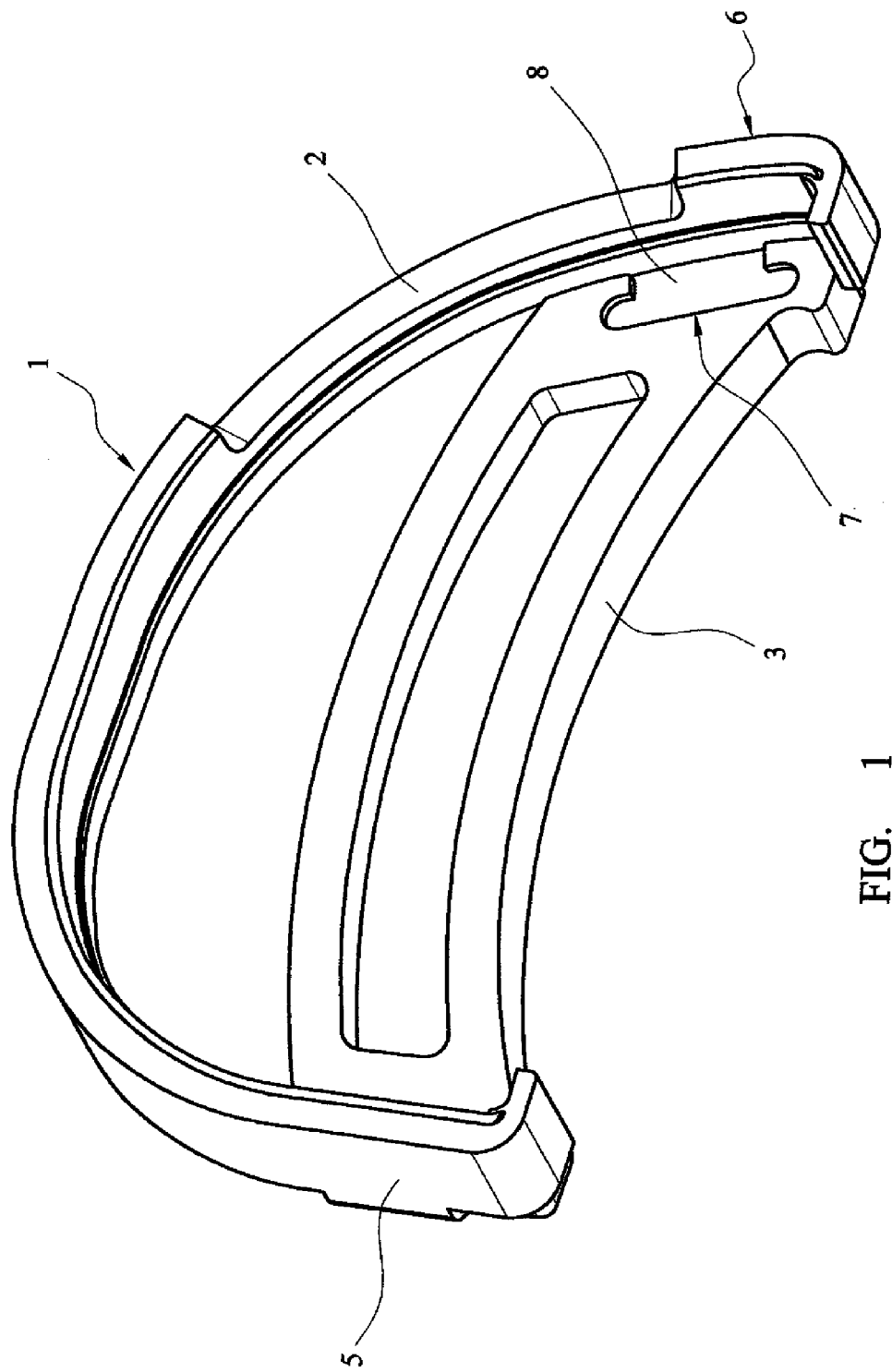
FIG. 1 shows the assembly of the present invention from an angle below the lower bone engaging surface planar surface of the tibial component.

Referring to the drawings FIG. 1 shows a skirt 1 having one aperture 2 in the anterior section of the skirt and a strap 3 prior to attaching the skirt 1 to the tibial component. The skirt 1 can be secured to the tibial component 4 of a unicondylar knee joint prosthesis using the strap 3. The strap 3 is attached to the posterior section 5 of the skirt 1 and extends across the upper surface of the tibial component 4 and attaches to the anterior section 6 of the skirt 1. The strap 3 has two opposing indents 7 in the two edges which make contact with the skirt 1. The skirt 1 has two protrusions 8, one in the posterior section 5 and one in the anterior section 6 of skirt 1, which insert into the opposing indents 7 of strap 3. The strap 3 has an opening 9 in the section of the strap extending across the upper surface of the tibial component 4 to increase its flexibility in this section. When prepared for implantation, the skirt 1 is located in contact with the edge of the tibial component 4. The skirt 1 extends beyond the edge of the unicondular tibial component 4 so that it contacts the tibial component 4 at the corners where the component abuts the intact tibial bone tissue of the other compartment of the knee joint. The strap 3 then extends across the upper surface of the unicondular tibial component 4. The indents 7 in the strap 3 will make contact with the protrusions 8 on opposing sides of the upper surface of the skirt. The skirt 1 is made from a rigid polymeric material such as polypropylene, with a coating on its inwardly facing surface silicone rubber. The aperture 2 in the anterior section 6 of the skirt 1 controls the flow of the excess bone cement from within the cavity 10 formed between the skirt and the lower surface of the tibial component 4 so that the bone cement flows anteriorly. The dimensions of the aperture 2 in the anterior section 6 of the skirt 1 are sufficient to subject the bone cement within the cavity 10 to be subjected to pressure and to also allow the excess bone cement to flow anteriorly at a desired rate.

After the tibial component 4 has been secured to the head of the bone and all of the excess bone cement has been removed from the joint region the skirt 1 is removed from the external edge of the tibial component by removing the strap 3.

Figure 2:
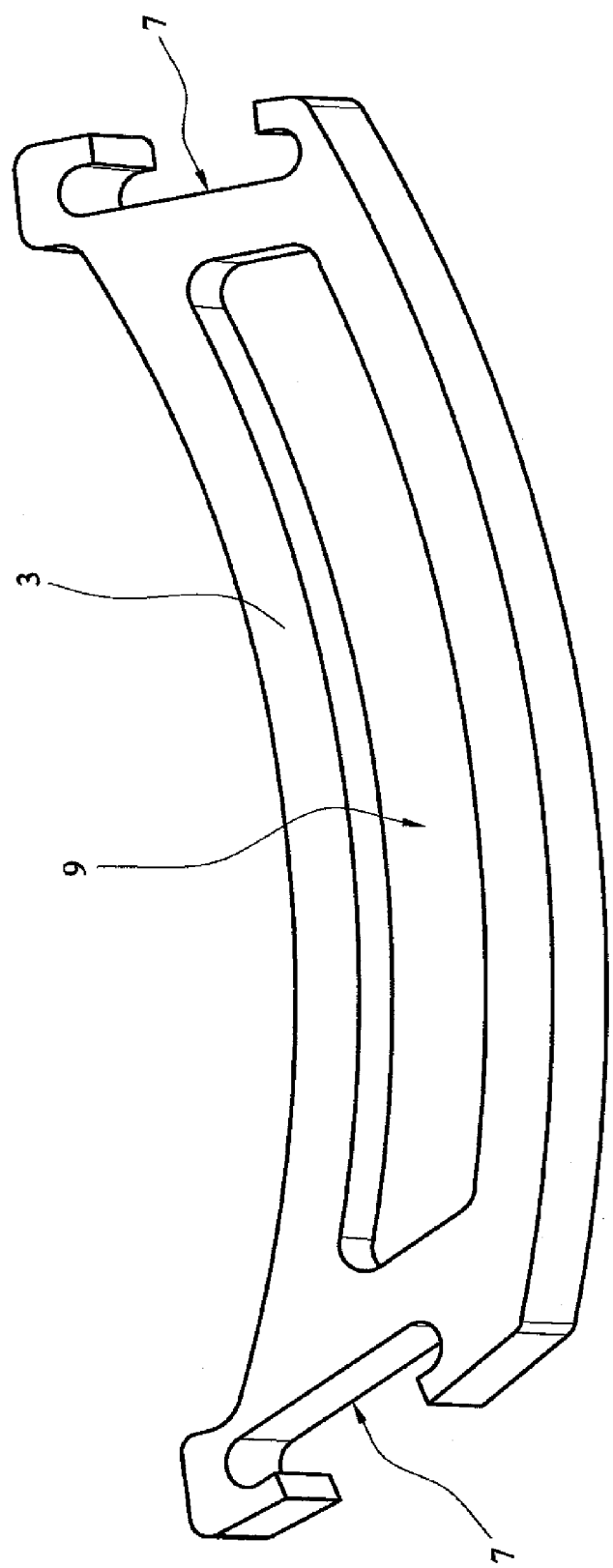
FIG. 2 shows the strap used to secure the skirt of to the tibial component.

FIG. 2 shows the strap 3 comprising two opposed indents 7 at opposing contact ends of the strap 3. Each indent 7 corresponds in shape to an opposingly shaped protrusion 8 on the upper surface of the skirt 1. The strap 3 has an opening 9 in the central section of the strap. The strap 3 can be made from a material such as a polyolefin.

Figure 3:
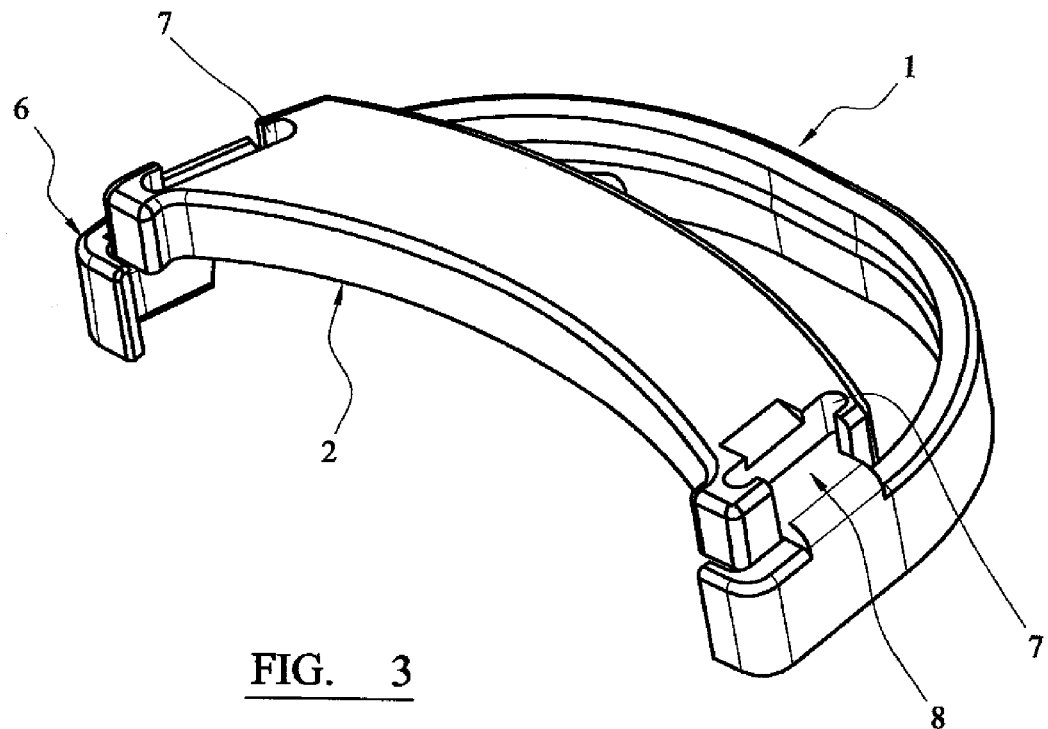
FIG. 3 shows the assembly of the present invention at an angle above the upper surface.

FIG. 3 shows the assembly of the present invention at an angle above the plane of the tibial component. The assembly comprises a skirt 1 in the shape of the edge of an tibial component 4 having one aperture 2 in the anterior section 6 of the skirt 1. The skirt 1 is to be secured to the tibial component 4 using a strap 3. The strap 3 has two opposing indents 7 corresponding to the shape of the protrusions 8 on the upper surface of the skirt 1. The protrusions 8 are inserted into the indents 7 to secure the skirt 1.

Figure 4:
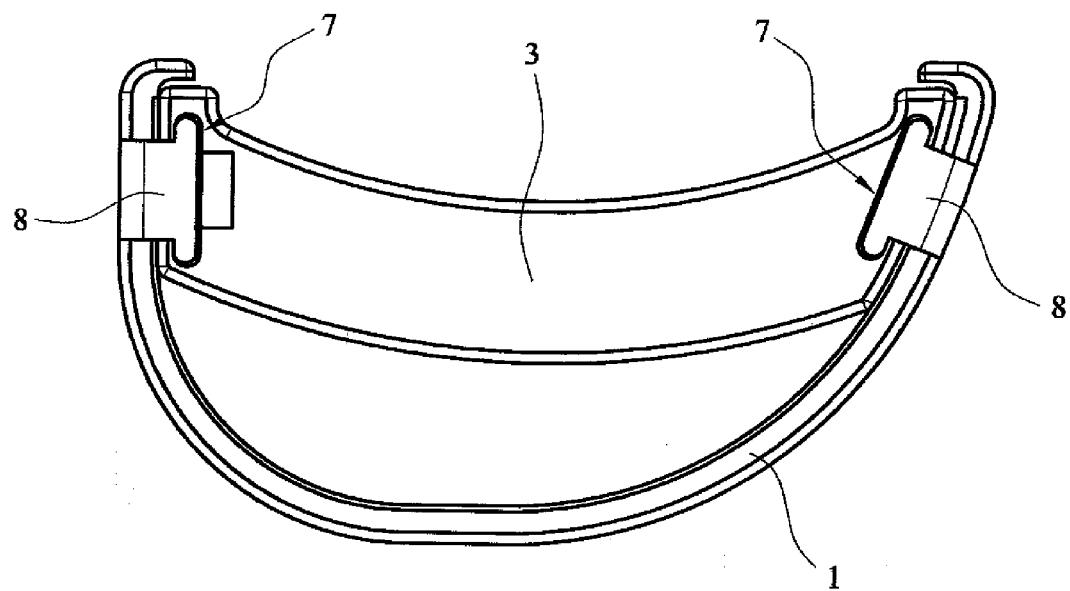
FIG. 4 shows the assembly of the present invention from directly above the upper surface of the tibial component.

FIG. 4 shows the assembly of the present invention from directly above the plane of the tibial component. The shape of the skirt 1 corresponds to the shape of the edge of the tibial component. The protrusions 8 on the upper surface of the skirt 1 are inserted into the indents 7 in opposing ends of the strap 3 so as to secure the skirt 1.

Figure 5:
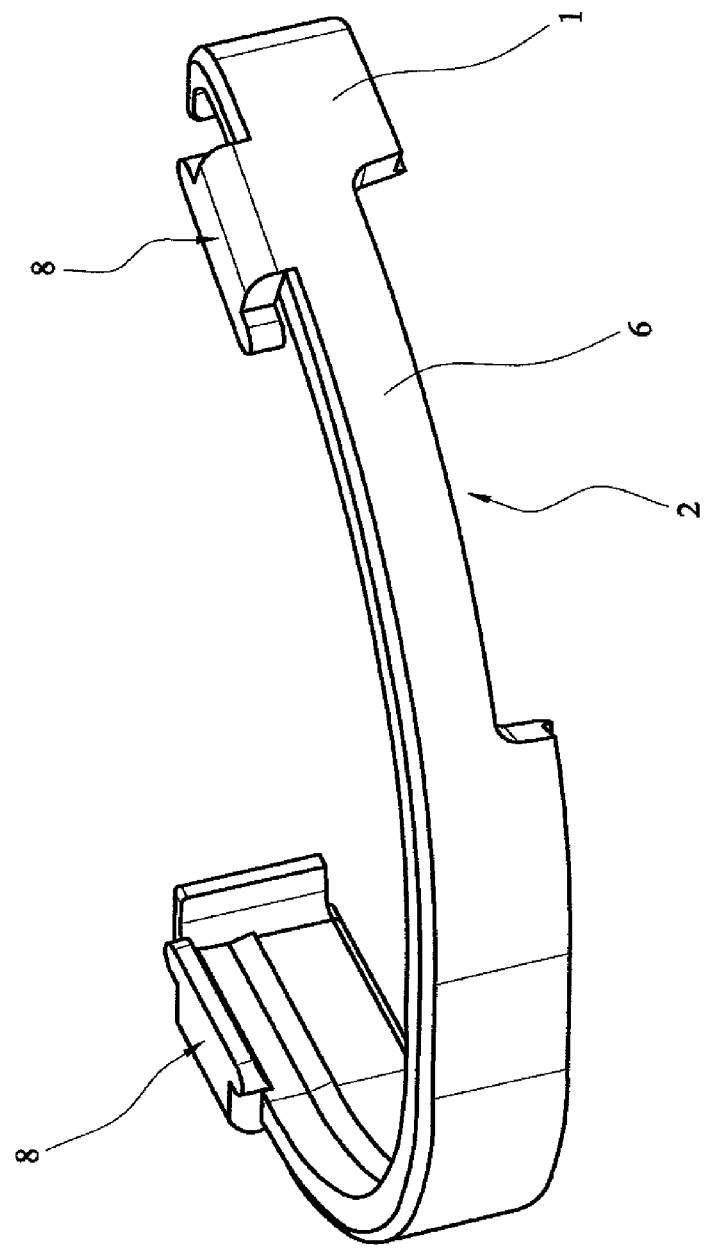
FIG. 5 shows the skirt of the present invention with an aperture in the anterior section of the skirt together with two opposing protrusions on the upper surface of the skirt.

FIG. 5 shows the skirt 1 of the present invention comprising an aperture 2 in the anterior section 6 of the skirt 1 together with two opposing protrusions 8 on the upper surface of the skirt.

Figure 6:
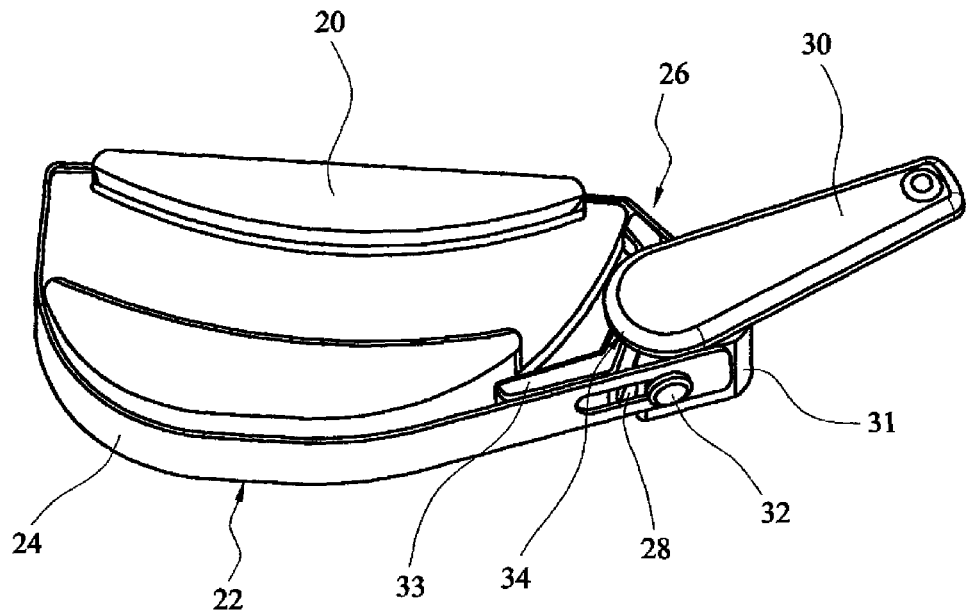
FIGS. 6 and 7 are perspective views of the superior faces of other assemblies according to the invention which comprise a unicompartmental tibial component with skirt which is provided a band and clamp arrangement.

FIG. 6 shows an assembly of a unicompartmental tibial component 20 and a skirt 22. The skirt comprises a band 24 and a clamp 26. The band is formed from a polypropylene material which is sufficiently flexible to enable it to be wrapped around the tibial component. The band has an elongate slot 28 (one only shown) at each end. The depth of the band is sufficient to extend beyond the bone facing surface of the tibial component.

The clamp 26 has a lever 30 which is mounted on a lever support 31 so that it can rotate relative to the support. The support has a pair of buttons 32 which can fit through respective ones of the slots 28 in the band with the lever 30 and the tibial component 20 within the skirt. Also located within the skirt is a support frame 33, located between the lever support and the edge of the tibial component. The lever has a bearing surface 34 (not visible in the drawing) which acts against the support frame 33. The bearing surface is generally rounded, but is arranged eccentrically relative to the fulcrum around which the lever rotates relative to the lever support 31. Rotation of the lever causes the point of action of the bearing surface against the support frame to move along the bearing surface. The eccentric arrangement of the lever means that the tension in the band changes as the lever is rotated.

Figure 7:
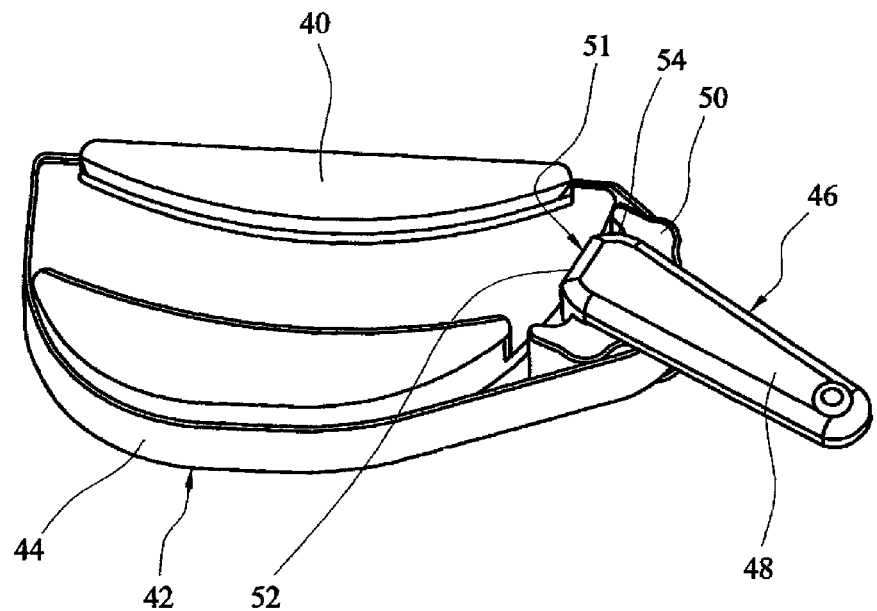

FIG. 7 shows another embodiment of an assembly of a unicompartmental tibial component 40 and a skirt 42, similar to that shown in FIG. 6. The skirt comprises a band 44 and a clamp 46. The band is continuous, extending around the tibial component and the clamp.

The clamp comprises a lever 48 and a lever support 50. The lever is mounted for pivotal movement on the support. The lever has a bearing surface 51 which acts against the edge of the tibial component 40. The bearing surface is provided in part by a flattened end 52 which, as shown in FIG. 7, acts against the edge of the tibial component 40 when the lever is in the position in which the band is loose. The bearing surface continues around a rounded corner 54.

Pivotal movement of the lever 48 relative to the support 50 causes the bearing surface 51 of lever to move relative to the edge of the tibial component, so that the rounded corner 54 contacts the edge of the tibial component. the rounded corner is located further from the fulcrum mount of the lever 48 on the lever support 50 so that the lever with its support are forced away from the tibial component as a result of rotation of the lever. This causes the band 44 to tighten.

In each of the embodiments shown in FIGS. 6 and 7, the skirt is located around the tibial component so that it extends beyond the bone engaging face of the component. The skirt therefore restricts the flow of cement from the space between the tibial component and a bone which it faces, around the entire periphery of the component apart from that region of the component where the clamp is located. In this region, there is effectively a gap in the skirt.

The component with the skirt is located on the bone with an appropriate quantity of cement located between the bone and the component. The band prevents displacement of cement from the space between the bone and the component at all points around the periphery of the component apart from that part of the periphery where the clamp is located. In this region, there is nothing to impede displacement of the cement. By appropriate orientation of the tibial component and the skirt relative to the bone (and to the incision through which the procedure is being performed), the skirt can direct the displaced cement so that the surgeon is able to collect it.

Once the cement has hardened (at least partially), the skirt is removed from the component. This is done by first releasing the clamp by rotating the lever to the loose position. The band and the lever can then be lifted off the tibial component. It might be preferred to open the band, which can be done by cutting it or, in the case of the band shown in FIG. 6, releasing it from the clamp by lifting a slot 28 in the band 24 off its respective button 32.

Figure 8:
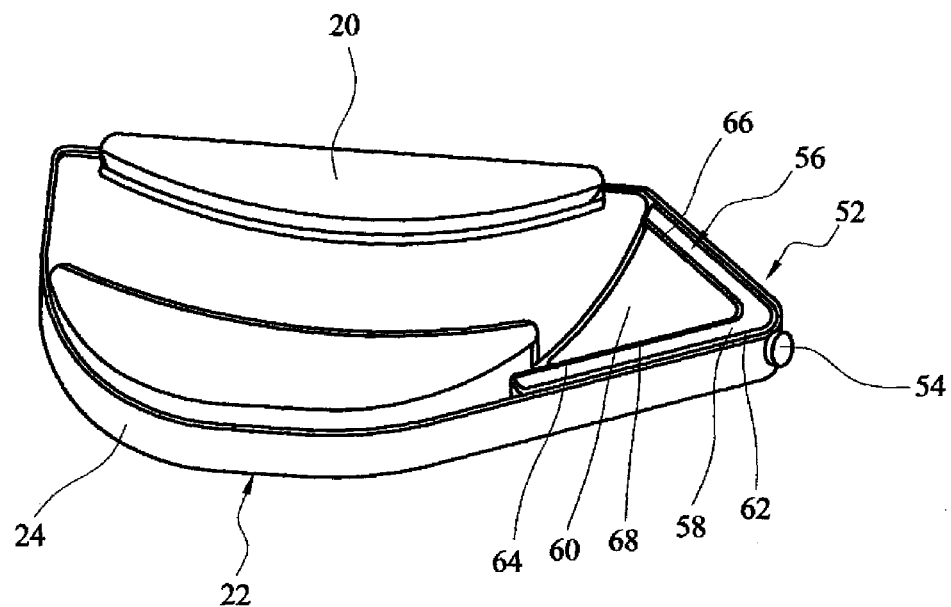
FIGS. 8 and 9 are perspective views of the superior faces of other assemblies according to the invention which comprise a unicompartmental tibial component with skirt which is provided a band and driver arrangement.
Figure 9:
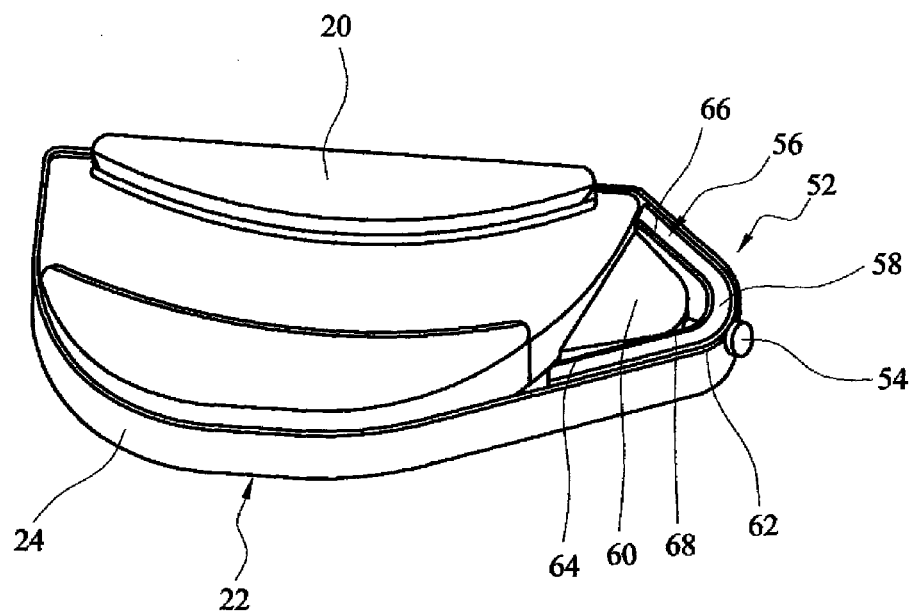

FIGS. 8 and 9 show an assembly of a unicompartmental tibial component 20 and a skirt 22. The skirt 22 comprises a band 24 and a driver arrangement 52. The driver arrangement 52 comprises an actuator 54 and an assembly 56 comprising a first block 58 and a second block 60.

The first block 58 has a curved outer surface 62 which is contacted by the band 24. The second block 60 has an inner surface 64 which contacts the unicompartmental tibial component 20. The first block 58 has an inner surface 66 which contacts the outer surface 68 of the second block 60. The inner surface 66 of the first block 58 is shaped so as to cooperatively engage the outer surface 68 of the second block 60.

A threaded bore extends through the first block 58 between its inner 66 and outer surfaces 62. The opening of the bore on the outer surface 62 of the first block 58 is aligned with an aperture in the band 24.

The actuator 54 comprises a threaded shaft and extends through the aperture in the band 24 into the threaded bore of the first block 58. The threaded shaft of the actuator 54 engages the threaded bore of the first block 58. The threaded shaft of the actuator 54 contacts the outer surface 68 of the second block 60.

In use, the shaft of the actuator 54 is rotated within the threaded bore of the first block 58 causing the first block 58 to advance along the shaft of the actuator 54 in the direction away from the unicompartmental tibial component 20.

The shaft of the actuator 54 contacts the outer surface 68 of the second block 60 and maintains contact between the unicompartmental tibial component 20 and the inner surface 64 of the second block 60.

The relative positions of the first block 58 and second block 60 prior to rotation of the actuator 54 is shown in FIG. 8. FIG. 9 illustrates the relative positions of the first member 58 and second member 60 after rotation of the actuator 54. Rotation of the driver 54 can therefore vary the separation between the first block 58 and the second block 60 and the tension in the band 24.

The invention claimed is:

1. An assembly for use in fixing a tibial component of a joint prosthesis to a prepared tibia, comprising:
   a tibial component having a bone facing surface, an exposed surface, and an edge having a posterior portion and an anterior portion; and
   a skirt having an interior surface, an exterior surface opposite the interior surface, at least one opening extending therethrough, and an inferior surface that can be temporarily fixed to the edge of the tibial component extending along the edge thereof from the posterior portion of the edge to the anterior portion of the edge;
   the skirt, when assembled with the tibial component, permits cement, located in the space defined at least in part by the interior surface of the skirt, the tibial component and the surface of the bone on which the tibial component is to be implanted, to be displaced through the opening to a location adjacent the exterior surface of the skirt, the at least one opening located so that cement is displaced at the anterior portion of the edge.

2. The assembly of claim 1, wherein the tibial component is a component of a unicompartmental knee joint prosthesis.

3. The assembly of claim 1, wherein the tibial component is a component of a total knee joint prosthesis.

4. An assembly for use in fixing a tibial component of a joint prosthesis to a prepared tibia, comprising:
- a tibial component having a bone facing surface, an exposed surface, and an edge having a posterior portion and an anterior portion; and
- a skirt comprising a band that has an interior surface, an exterior surface opposite the interior surface, at least one opening extending therethrough, and the inferior surface that can be temporarily fixed to the edge of the tibial component extending along the edge thereof from the posterior portion of the edge to the anterior portion of the edge;

when the skirt is assembled with the tibial component, cement located in the space defined at least in part by the interior surface of the skirt, between the bone facing surface of the tibial component and the surface of the bone on which the tibial component is to be implanted is displaceable through the at least one opening at the anterior portion of the edge to a location adjacent the exterior surface of the skirt.

* * * * *